United States Patent [19]

Wollensak et al.

[11] 4,066,562

[45] Jan. 3, 1978

[54] ANTIOXIDANT

[75] Inventors: John C. Wollensak, Bloomfield Hills; Kryn G. Ihrman, Farmington, both of Mich.; Paul G. Elsey, Baton Rouge, La.

[73] Assignee: Ethyl Corporation, Richmond, Va.

[21] Appl. No.: 722,324

[22] Filed: Sept. 10, 1976

[51] Int. Cl.$^2$ .................. C07C 39/16; C01M 1/54
[52] U.S. Cl. ..................... 252/52 R; 208/15; 208/18; 208/20; 252/404; 260/45.95 H;398.5;619 A; 426/268; 426/546; 426/601; 426/623; 426/635
[58] Field of Search ............... 426/636; 260/619 A, 260/45.95 R, 45.95 B, 398.5; 208/15, 18, 20; 252/404, 52 R; 426/268, 546, 601, 623, 635, 636

[56] References Cited

U.S. PATENT DOCUMENTS

| | | | |
|---|---|---|---|
| 2,732,406 | 1/1956 | Lambert | 260/619 A |
| 2,732,407 | 1/1956 | Lambert et al. | 260/619 A |
| 2,903,493 | 9/1959 | Lambert et al. | 260/619 A |
| 2,976,260 | 3/1961 | Newland et al. | 260/619 A |
| 3,000,856 | 9/1961 | Newland et al. | 260/619 A |

*Primary Examiner*—Norman Morgenstern
*Attorney, Agent, or Firm*—Donald L. Johnson; Robert A. Linn; Joseph D. Odenweller

[57] ABSTRACT

Methylenebis(dicyclopentyl phenols) in which at least one cyclopentyl group is ortho to the phenolic hydroxy group are effective antioxidants in a broad range of organic materials including mineral and synthetic lubricating oil and polyolefins.

16 Claims, No Drawings

ANTIOXIDANT

BACKGROUND

Methylenebis(dialkylphenols) are known antioxidant compounds (U.S. Pat. No. 2,944,086). Likewise, dicyclopentyl phenols have been reported to be antioxidants (West German OLS No. 2,527,402).

SUMMARY

According to the present invention new compounds are provided which are methylene-bridged dicyclopentyl phenols. These new compounds are effective antioxidants in a broad range of organic substrates normally subject to gradual oxidative degradation in storage or use.

DESCRIPTION OF THE PREFERRED EMBODIMENTS

A preferred embodiment of this invention is an antioxidant compound or mixture of compounds having the formula

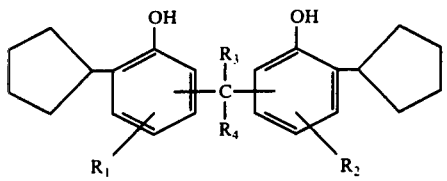

wherein $R_1$ and $R_2$ are cyclopentyl groups and are bonded to their respective phenolic benzene rings at a location independently selected from the ortho and para positions, the methylene bridge being connected between the remaining ortho and para positions, and $R_3$ and $R_4$ are independently selected from the group consisting of hydrogen and $C_{1-4}$ alkyl.

In making the compounds a minor amount of product is obtained in which $R_1$ and $R_2$ is in the meta position, generally opposite the other cyclopentyl group. In this case the methylene bridge can bond to either the open ortho or para position.

The term "methylene bridged" is used to include compounds in which the methylene bridge is alkyl substituted. Examples of these compounds are 4,4'-methylenebis(2,6-dicyclopentyl phenol), 2,2'-methylenebis(4,6-dicyclopentyl phenol), 2,4-dicyclopentyl-6-(3,5-dicyclopentyl-4-hydroxybenzyl)phenol, 4,4'-ethylidenebis(2,6-dicyclopentyl phenol), 2,2'-ethylidenebis(4,6-dicyclopentyl phenol), 4,4'-isopropilidenebis(2,6-dicyclopentyl phenol), 4,4'-pentylidenebis(2,6-dicyclopentyl phenol), 2,4-dicyclopentyl-6-[1-(3,5-dicyclopentyl-4-hydroxyphenol)-1-methylpropyl]phenol, 2,4-dicyclopentyl-6-[1-(3,5-dicyclopentyl-4-hydroxyphenyl)-1-butylpentyl]phenol, and the like.

The preferred antioxidants are 4,4'-methylenebis(2,6-dicyclopentyl phenol), 2,2'-methylenebis(4,6-dicyclopentyl phenol), 2,4-dicyclopentyl-6-(3,5-dicyclopentyl-4-hydroxybenzyl) phenol and mixtures of the foregoing.

The starting dicyclopentyl phenol can be made by the alkylation of phenol with cyclopentene under well-known alkylation conditions. Useful catalysts include sulfuric acid, phosphoric acid, aluminum chloride, boron fluoride, zinc chloride, stannic chloride and the like. Such acid or Friedel-Crafts catalyst give mixtures containing both 2,6-dicyclopentyl phenol and 2,4-dicyclopentyl phenol and very minor amounts of 2,5-dicyclopentyl phenol. These may be separated and used independently to prepare the desired product or the product may be made from a mixture of these dicyclopentyl phenols.

In a preferred embodiment the starting material is predominantly 2,6-dicyclopentyl phenol. This compound can be made in high yield by reacting phenol with cyclopentene in contact with an aluminum phenoxide catalyst according to the process taught by Ecke et al, U.S. Pat. No. 2,831,898, incorporated herein by reference.

According to Ecke et al granular aluminum is reacted with phenol under anhydrous conditions to form a catalytic amount of aluminum phenoxide in the phenol. An aluminum:phenol mole ratio of 1:5 to 1:20 is useful. Cyclopentene is reacted with the phenol in an autoclave at about 200° to 300° C. for up to 24 hours. Following this the reaction mixture is washed with aqueous acid to remove aluminum. The 2,6-dicyclopentyl phenol is recovered by distillation.

The dicyclopentyl phenol, either 2,4- or 2,6- or mixtures thereof which may also contain minor amounts of 2,5-dicyclopentyl phenol, is alkylene bridged by reaction with an aldehyde or ketone. Examples of such reactants are formaldehyde, acetaldehyde, butyraldehyde, acetone, methylethyl ketone, butylmethyl ketone, and the like. The preferred reactant is formaldehyde which may be used in the form of paraformaldehyde, aqueous formaldehyde or in the form of any formaldehyde-producing compound.

The reaction is conducted in the presence of an acid or basic catalyst. The preferred catalyst are basic catalysts such as the alkali metal hydroxides. Of these, the preferred hydroxide is potassium hydroxides.

The reaction is preferably carried out in a solvent. The preferred solvents are the lower, secondary, or tertiary alkanols. The preferred alkanols are isopropanol and tert-butyl alcohol, most preferably isopropanol.

About 1–1.5 moles of aldehyde or ketone are used per 2 moles of dicyclopentyl phenol. The amount of solvent should be the amount which is required to dissolve the reactants and the catalyst. Generally, about 0.5 to 2.5 parts of solvent per part of 2,6-dicyclopentyl phenol is adequate.

The amount of catalyst should be an amount which causes the reaction to proceed at a reasonable rate. A useful catalyst concentration is about 0.02 to 1.0 moles of catalyst per mole of dicyclopentyl phenol. Under these conditions the reaction is usually complete in about 1–4 hours.

The product may be recovered by conventional means such as crystallization, filtration, vacuum distillation or solvent extraction. Optionally the reaction mixture may be washed to remove solvent, catalyst and unreacted dicyclopentyl phenol and used in crude form as an antioxidant.

The following examples illustrate the manner of preparing the novel antioxidants.

EXAMPLE 1

In an autoclave was placed 376.4 grams (4 moles) of phenol and 3.27 grams (.12 moles) of granular aluminum. The clave was sealed, flushed with nitrogen and heated to 222° C. A reaction started and temperature rose to 236° C. over a 45-minute period. It was then cooled and vented (caution hydrogen). The vessel was then heated to 243° C. and 311 grams of cyclopentene was pumped in over a 55-minute period at 243°–257° C.

(100–125 psig). Reaction was continued for 4 hours at 242°–247° C. An additional 58 grams of cyclopentene was pumped in at 230°–232° C. over 9 minutes. Reaction was continued at 230°–255° C. for 2 hours, 40 minutes. The clave was then cooled to 90° C. and vented. The product was washed with 25% aqueous HCl to remove aluminum catalyst and then distilled to recover dicyclopentyl phenol (178°–183° C. at 4–4.25 mm Hg).

EXAMPLE 2

In a reaction vessel was placed 55 grams (0.25 moles) of 2,6-dicyclopentyl phenol, 100 ml isopropanol, 11.3 grams of 37% aqueous formaldehyde (0.137 mole) and 1.2 grams 85% KOH. The vessel was purged with nitrogen and stirred at 50°–60° C. for 11 hours, 10 minutes. The mixture was washed with water to remove catalyst and solvent and then stripped of volatiles under aspiration vacuum while heating in a steam bath. The final product was a resinous material at room temperature. On standing the material crystallized. The crystals were identified as 4,4'-methylenebis(2,6-dicyclopentyl phenol) by NMR.

The other compounds of this invention can be prepared by similar methods. Alkylation of phenol using Friedel-Crafts (e.g., $AlCl_3$, $BF_3$) or acid (e.g., $H_2SO_4$, $H_3PO_4$) catalyst will give both 2,4- and 2,6-dicyclopentyl phenol and minor amounts of 2,5-dicyclopentyl phenol. Such alkylation reactions are well known. The components may be separated by distillation and used individually to prepare the various methylenebis dicyclopentyl phenol derivatives. Alternatively, mixtures of both 2,4- and 2,6-dicyclopentyl phenol may be used to give a mixture of methylenebis dicyclopentyl phenols.

Other aldehydes or ketones may be substituted for the formaldehyde used in Example 2 to form the corresponding derivative in which the methylene bridge is alkyl substituted. These include acetaldehyde, butyraldehyde, valeraldehyde, acetone, methylethyl ketone and the like. Such procedures are known in the art such as Zaweski, U.S. Pat. No. 3,367,980, incorporated herein by reference.

The methylenebis dicyclopentyl phenols are effective stabilizers in a broad range of organic materials of the type normally subject to oxidative deterioration in the presence of oxygen during use over an extended period. In other words, the organic compositions protected by the present antioxidants are the type in which the art recognizes the need for antioxidant protection and to which an antioxidant of some type is customarily added to obtain an extended service life. The oxidative degradation protected against is the slow gradual deterioration of the organic composition rather than, for example, combustion. In other words, the present additives are not flame retarding additives nor flame suppressing additives and the degradation protected against is not combustion but, rather, the gradual deterioration of the organic composition due to the effects of oxygen over an extended period of time.

Examples of organic materials in which the additives are useful include polymers, both homopolymers and copolymers, of olefinically unsaturated monomers, for example, polyolefins such as polyethylene, polypropylene, polybutadiene, and the like. Also, poly-halohydrocarbons such as polyvinyl chloride, polychloroprene, polyvinylidene chloride, polyfluoro olefins, and the like, are afforded stabilization. The additives provide both antioxidant and antiozonant protection in natural and synthetic rubbers such as copolymers of olefinically unsaturated monomers including styrene-butadiene rubber (SBR rubber), ethylenepropylene copolymers, ethylene-propylene-diene terpolymers such as the terpolymer of ethylene, propylene and cyclopentadiene or cyclooctadiene. Polybutadiene rubbers such as cis-polybutadiene rubber are protected. Poly-2-chloro-1,3-butadiene (neoprene) and poly-2-methyl-1,3-butadiene (isoprene rubber) are stabilized by the present additives. Likewise, acrylonitrilebutadiene-styrene resins are effectively stabilized. Ethylenevinyl acetate copolymers are protected, as are butene-methylacrylate copolymers. Nitrogen-containing polymers such as polyurethanes, nitrile rubber, and lauryl acrylate-vinylpyrrolidone copolymers are effectively stabilized. Adhesive compositions such as solutions of polychloroprene (neoprene) in toluene are protected.

Fats and oils of animal and vegetable origin are protected against gradual deterioration. Examples of these are lard, beef tallow, coconut oil, safflower oil, castor oil, babassu oil, cottonseed oil, corn oil, rapeseed oil, and the like.

Petroleum oils and waxes such as solvent-refined, midcontinent lubricating oil, microcrystalline wax, and Gulfcoast lubricating oils are effectively stabilized.

Animal feeds such as ground corn, cracked wheat, oats, wheat germ, alfalfa, and the like, are protected by mixing a small but effective amount of the present additive with these products. Vitamin extracts, especially the fat-soluble vitamins such as Vitamin A, B, D, E and C, are effectively stabilized against degradation.

The additives are useful in foamed plastics such as expanded polystyrene, polyurethane foams, and the various foamed rubbers, alkyd resins such as short oil terephthalic acid-glycerol-linseed oil resins, and typical long oil resins of trimellitic acid-glycol-tung oil resins including epoxide-modified alkyl resins. Epoxy resins themselves such as isopropylidenebisphenolepichlorohydrin epoxy resins are stabilized against degradation.

Hydrocarbons such as gasoline, kerosene, diesel fuel, fuel oil, furnace oil, and jet fuel are effectively protected. Likewise, synthetic hydrocarbon lubricants, for example, α-decene trimer, polybutene lubricants, di- and tri-$C_{12-30}$ alkylated benzene and naphthalene synthetic lubricants are likewise protected.

Organometallics such as tetraethyllead, tetramethyllead, tetravinyllead, ferrocene, methyl ferrocene, cyclopentadienyl manganese tricarbonyl, methyl cyclopentadienyl manganese tricarbonyl, cyclopentadienyl nickel nitrosyl, and the like, are effectively protected against oxidative degradation. Silicone oils and greases are also protected.

Synthetic ester lubricants such as those used in turbines and turbojet engines are given a high degree of stabilization. Typical synthetic ester lubricants include di-2-ethylhexyl sebacate, trimethylolpropane tripelargonate, $C_{5-9}$ aliphatic monocarboxylic esters of pentaerythritol, complex esters formed by condensing under esterifying conditions mixtures of polyols, polycarboxylic acids, and aliphatic monocarboxylic acids and/or monohydric alkanols. An example of these complex esters is the condensation product formed from adipic acid, ethyleneglycol and a mixture of $C_{5-9}$ aliphatic monocarboxylic acids. Plasticizers such as dioctyl phthalate are effectively protected. Heavy petroleum fractions such as tar and asphalt can also be protected should the need arise.

Polyamides such as adipic acid-1,6-diaminohexane condensates and poly-6-aminohexanoic acid (nylon) are effectively stabilized. Polyalkylene oxides such as copolymers of phenol with ethylene oxide or propylene oxide are stabilized. Polyphenyl ethers such as poly-2,6-dimethylphenyl ether formed by polymerization of 2,6-dimethylphenol using a copper-pyridine catalyst are stabilized. Polycarbonate plastics and other polyformaldehydes are also protected.

Linear polyesters such as phthalic anhydride-glycol condensates are given a high degree of protection. Other polyesters such as trimellitic acid-glycerol condensates are also protected. Polyacrylates such as polymethylacrylate and polymethylmethacrylate are effectively stabilized. Polyacrylonitriles and copolymers of acrylonitriles with other olefinically unsaturated monomers such as methylmethacrylates are also effectively stabilized.

The additives can be used to protect any of the many organic substrates to which an antioxidant is normally added. It can be used where economics permit to protect such substrates as asphalt, paper, fluorocarbons such as teflon, polyvinyl acetate, polyvinylidene chloride, coumarone-indene resins, polyvinyl ethers, polyvinylidene bromide, polyvinyl bromide, acrylonitrile, vinyl bromide copolymer, vinyl butyral resins, silicones such as dimethylsilicone lubricants, phosphate lubricants such as tricresylphosphate, and the like.

The additives are incorporated into the organic substrate in a small but effective amount so as to provide the required antioxidant protection. A useful range is from about 0.01 to about 5 weight percent, and a preferred range is from about 0.1 to 3 weight percent.

Methods of incorporating the additive into the substrate are well known. For example, if the substrate is liquid the additive can be merely mixed into the substrate. Frequently the organic substrate is in solution and the additive is added to the solution and the solvent removed. Solid organic substrates can be merely sprayed with a solution of the additive in a volatile solvent. For example, stabilized grain products result from spraying the grain with a toluene solution of the additive. In the case of rubbery polymers the additive can be added following the polymerization stage by mixing it with the final emulsion or solution polymerization mixture and then coagulating or removing solvent to recover the stabilized polymer. It can also be added at the compounding stage by merely mixing the additive with the rubbery polymer in commercial mixing equipment such as a Banbury blender. In this manner, rubbery polymers such as styrene-butadiene rubber, cis-polybutadiene or isoprene polymers are blended with the antioxidant together with the other ingredients normally added such as carbon black, oil, sulfur, zinc oxide, stearic acid, vulcanization accelerators, and the like. Following mastication, the resultant mixture is fabricated and molded into a finished form and vulcanized. The following will serve to illustrate the manner in which the additives are blended with various organic substrates. The following describes organic compositions containing the additives of the present invention. Additives are designated as follows:

A - 4,4'-methylenebis(2,6-dicyclopentylphenol)
B - 2,2'-methylenebis(4,6-dicyclopentylphenol)
C - 2,4-dicyclopentyl-6-(3,5-dicyclopentyl-4-hydroxyphenylmethyl)phenol
D - 4,4'ethylidenebis(2,6-dicyclopentylphenol)
E - 4,4'-isopropylidenebis(2,6-dicyclopentylphenol)
F - 4,4'-pentylidenebis(2,6-dicyclopentylphenol)
G - 4,4'-(1-butylpentylidene)bis(2,6-dicyclopentylphenol)
H - 4,4'-(1-methylpropylidene)bis(2,6-dicyclopentylphenol)
I - 2,2'-isopropylidenebis(4,6-dicyclopentylphenol)
J - 2,2'-(1-methylpropylidene)bis(4,6-dicyclopentylphenol)
K - 2,2'-pentylidenebis(4,6-dicyclopentylphenol)
L - 2,4-dicyclopentyl-6-[1-(3,5-dicyclopentyl-4-hydroxyphenyl)ethyl]phenol
M - 2,4-dicyclopentyl-6-[3,5-dicyclopentyl-4-hydroxyphenyl)-1-methylethyl]phenol
N - 2,4-dicyclopentyl-6-[1-(3,5-dicyclopentyl-4-hydroxyphenyl)-pentyl]phenol

EXAMPLE 3

To a synthetic rubber master batch comprising 100 parts of SBR rubber having an average molecular weight of 60,000, 50 parts of mixed zinc propionate stearate, 50 parts carbon black, 5 parts road tar, 2 parts sulfur and 1.5 parts of mercapto benzothiazole is added 1.5 parts of additive A. After mastication, the resultant master batch is cured for 60 minutes using 45 psi steam pressure, resulting in a stabilized SBR vulcanizate.

EXAMPLE 4

A synthetic SBR polymer is prepared by polymerizing 60 percent styrene and 40 percent butadiene in an aqueous emulsion employing a sodium oleate emulsifier and a peroxide catalyst. Following this, sufficient additive B is added to produce 0.3 weight percent, based upon the SBR polymer. The emulsion is then coagulated using an acidified salt solution and the coagulated polymer compressed into bales for storage. The polymer is stable during storage and can later be compounded to prepare SBR vulcanizates.

EXAMPLE 5

One part of additive C is blended with 100 parts of raw butyl rubber prepared by the copolymerization of 90 percent isobutylene and 10 percent isoprene, resulting in a stable elastomer.

EXAMPLE 6

A cis-polybutadiene polymer is prepared having 90 percent cis configuration by polymerizing butadiene in a toluene solvent employing a diethyl aluminum chloride-cobalt iodide catalyst. Following the polymerization, a small amount sufficient to provide 0.2 weight percent of additive D is added to the toluene solution, following which the solution is injected into boiling water together with steam causing the solvent to distill out and the cis-polybutadiene to coagulate, forming a rubber crumb. The crumb is dried and compressed into bales, resulting in a stabilized cis-polybutadiene.

EXAMPLE 7

A butadiene-acrylonitrile copolymer is prepared from 1,3-butadiene and 32 percent of acrylonitrile. One percent, based on the weight of polymer, of additive E is added as an emulsion in a sodium oleate solution. The latex is coagulated and the coagulum is washed and dried, resulting in a stabilized butadiene-acrylonitrile copolymer.

EXAMPLE 8

To 1,000 parts of a solid polypropylene powder is added 5 parts of additive F and 10 parts of dilaurylthiodipropionate. The mixture is heated to its melting point and rapidly stirred and extruded to form a useful polypropylene filament.

EXAMPLE 9

To 1,000 parts of polyethylene is added 3 parts of additive G and 5 parts of dilaurylthiodipropionate. The mixture is heated to its melting point and stirred and then passed through an extruder having a central mandrel to form tubular polyethylene which is inflated to form a useful polyethylene film.

EXAMPLE 10

To 100,000 parts of a midcontinent, solvent-refined, mineral oil having a viscosity at 100° F. of 373.8 SUS and at 210° F. of 58.4 SUS is added 500 parts of additive H. Following this is added 100 parts of a zinc dialkyldithiophosphate, 50 parts of an overbased calcium alkaryl sulfonate, 1,000 parts of a poly dodecylmethacrylate V.I. improver and 2,000 parts of a 70 percent active oil solution of an alkenyl succinimide of tetraethylenepentamine in which the alkenyl group has a molecular weight of 950. The resultant mixture is blended while warm, following which it is filtered and packaged, giving a stable lubricating oil useful in automotive engines.

EXAMPLE 11

To 10,000 parts of a dimethyl silicone lubricating oil is added 50 parts of additive I. The mixture is stirred at 50° C. until thoroughly blended, resulting in a stable silicone lubricating oil.

EXAMPLE 12

To 10,000 parts of corn oil is added 15 parts of additive A. The mixture is stirred, giving a corn oil highly resistant to normal oxidative degradation.

EXAMPLE 13

To 10,000 parts of trimethylolpropane tripelargonate is added 200 parts of tricresylphosphate, 10 parts of dimethyl silicone, 10 parts of benzothiazole, 50 parts of phenyl-$\beta$-naphthyl amine, and 50 parts of additive J, resulting in a stabilized synthetic ester lubricant.

EXAMPLE 14

Wax paper is made by impregnating paper with paraffin wax containing 0.05 weight percent of a mixture of additive K. The wax paper is used to make containers for potato chips which results in chips having extended shelf life.

EXAMPLE 15

To 10,000 parts of gasoline having an 87 R.O.N. is added 20 parts of additive L and sufficient commercial tetraethyllead antiknock fluid to provide 2.5 grams of lead per gallon, resulting in a stabilized gasoline having a 96 R.O.N.

EXAMPLE 16

To 10,000 parts of 41 cetane diesel fuel is added 50 parts of hexyl nitrate and 25 parts of additive M, providing a stable diesel fuel.

EXAMPLE 17

To 10,000 parts of melted lard is added 10 parts of additive N and the mixture is stirred until thoroughly blended, resulting in a lard highly resistant to normal oxidative degradation.

From the foregoing, it is apparent how to prepare stable organic compositions using the additives of this invention.

The antioxidants of this invention may be used alone as the sole antioxidant or may be used in combination with other antioxidants or compounds which synergistically affect the effectiveness of the antioxidant. Examples of other antioxidants include 4,4'-methylenebis(2,6-di-tert-butylphenol), 1,3,5-tri-methyl-2,4,6-tri(3,5-di-tert-butyl-4-hydroxybenzyl)benzene, 2,6-dicyclopentyl-4-methylphenol, 4,4'-thiobis(6-tert-butyl-m-cresol) 4,4'-butylidenebis(6-tert-butyl-m-cresol) $\beta$-(3,5-di-tert-butyl-4-hydroxy phenyl) propionic acid pentaerythritol ester and the like.

Particularly preferred synergists are the dialkylthiodipropionates such as dilauryl-thio-dipropionate and distearyl-thio-dipropionate. Such synergists are particularly effective in polyolefin (e.g., polypropylene) compositions and are used in concentrations of about 0.05 to about 0.3 weight percent.

Other synergists are dialkyl phosphites (e.g., dibutylphosphite, trialkyl phosphites (e.g., tributylphosphite), dialkyl tin sulfides (e.g., dibutyl tin sulfides (and the like.

Tests have been conducted which demonstrate the effectiveness of the present antioxidants.

Tests were carried out to demonstrate the antioxidant properties of the additives. In these tests 25 mil sheets of polypropylene were molded containing the additives. Five representatives of each are included. They are aged in an oven at 150° C. Failure is indicated by cracking, crazing or powdering on the surface of 3 of the 5 replicates.

One non-additive blank was included as well as one containing a dilauryl thiodipropionate (DLTDP) synergist. The results were as follows:

| | Additive | Conc. (wt %) | Hours to Failure |
|---|---|---|---|
| 1. | blank | — | 3 |
| 2. | 4,4'-methylenebis 2,6-dicyclopentyl- phenol | 0.1 | 48 |
| 3. | " | 0.3 | 144 |
| 4. | " plus DLTDP | 0.1 0.2 | 528 |

As the above results show the new additives are very effective antioxidants and respond well to synergists.

We claim:

1. An antioxidant compound or mixture of compounds having the formula

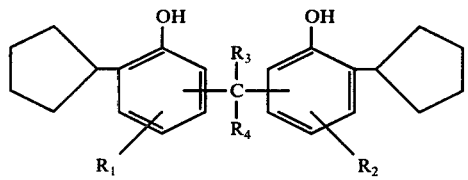

wherein $R_1$ and $R_2$ are cyclopentyl groups and are bonded to their respective phenolic benzene rings at a location independently selected from the ortho and para positions, the methylene bridge being connected between the remaining ortho and para positions, and $R_3$ and $R_4$ are independently selected from the group consisting of hydrogen and $C_{1-4}$ alkyl.

2. A compound of claim 1 wherein $R_3$ and $R_4$ are hydrogen.

3. The compound of claim 2, namely, 4,4'-methylenebis(2,6-dicyclopentyl phenol).

4. The compound of claim 2, namely, 2,2'-methylenebis(4,6-dicyclopentyl phenol).

5. The compound of claim 2, namely, (3,5-dicyclopentyl-4-hydroxy phenyl) (3,5-dicyclopentyl-2-hydroxy phenyl) methane.

6. Organic material normally subject to gradual oxidative deterioration in the presence of air containing an antioxidant amount of a compound of claim 1.

7. A composition of claim 6 wherein $R_3$ and $R_4$ are hydrogen.

8. A composition of claim 7 wherein said organic material is a normally liquid hydrocarbon.

9. A composition of claim 8 wherein said liquid hydrocarbon is lubricating oil.

10. A composition of claim 6 wherein said organic material is a polymer of an ethylenically unsaturated monomer.

11. A composition of claim 7 wherein said organic material is a polymer of an olefinically unsaturated monomer.

12. A composition of claim 11 wherein said polymer is polypropylene.

13. A composition of claim 11 wherein said polymer is polyethylene.

14. A composition of claim 6 wherein said organic material is a synthetic rubber.

15. A composition of claim 7 wherein said organic material is synthetic rubber.

16. A composition of claim 15 wherein said synthetic rubber is a polybutadiene.

* * * * *